(12) United States Patent
Hughes (10) Patent No.: US 6,799,123 B2
(45) Date of Patent: Sep. 28, 2004

(54) DISSOLUTION TEST EQUIPMENT AND METHOD

(76) Inventor: Lyn Hughes, 1740 Old Skippack Rd., Harleysville, PA (US) 19438

( * ) Notice: Subject to any disclaimer, the term of this patent is extended or adjusted under 35 U.S.C. 154(b) by 143 days.

(21) Appl. No.: 10/007,144

(22) Filed: Nov. 5, 2001

(65) Prior Publication Data

US 2003/0088369 A1 May 8, 2003

(51) Int. Cl.[7] .............................................. G06F 1/025
(52) U.S. Cl. ............................. 702/25; 702/22; 702/24; 702/50
(58) Field of Search ............................. 702/22, 24, 50, 702/109, 121, 25, 125, 175, 176, 198; 435/21; 514/338; 424/427

(56) References Cited

U.S. PATENT DOCUMENTS

| | | | | |
|---|---|---|---|---|
| 4,335,438 A | * | 6/1982 | Smolen | ....................... 364/497 |
| 5,983,515 A | * | 11/1999 | Brinker et al. | ................. 33/810 |
| 6,174,497 B1 | * | 1/2001 | Roinestad et al. | ........ 422/82.05 |
| 6,542,858 B1 | * | 4/2003 | Grass et al. | .................... 703/2 |

* cited by examiner

*Primary Examiner*—Marc S. Hoff
*Assistant Examiner*—Felix Suarez

(57) ABSTRACT

The present invention provides an apparatus for conducting dissolution tests. The apparatus includes two or more chambers connected in series; a supply of one or more media that can be continuously passed into the chambers; an analyzer of the effluent from the chambers for substances of interest in the test; and, a temperature controller for controlling the temperature of the medium in the chambers. The first chamber is capable of transferring solid particles to the second chamber. The second chamber is capable of retaining solid. The chambers have a means of adding test materials. The chambers have a means of mixing the sample and medium; and a means of analyzing the effluent can be carried out at multiple times during the operation of the test equipment.

3 Claims, 5 Drawing Sheets

Fig. 7

DISSOLUTION TEST EQUIPMENT AND METHOD

BACKGROUND

The rate at which pharmaceutically active compounds dissolve in gastrointestinal fluids is of crucial importance in the design and use of orally administered medications. The active compound must be dissolved before it can be absorbed by the body. The rate at which the active substance enters into solution is know in the art as the dissolution rate, and the determination of the dissolution rate in vitro is known as dissolution testing.

The concept of using in vitro data to predict or model in vivo behavior, referred to as in vitro—in vivo correlation, or IVIVC, is of great interest to the pharmaceutical arts. Test methods with good IVIVC are much more capable of detecting problems with existing formulations and in the development of new formulations. Systems which correlate closely with the dissolution and absorption data obtained in vivo can be used in developing dosage forms as well as in the production, scale-up, determination of lot-to-lot variability, testing of new dosage strengths, testing of minor formulation changes, testing after changes in the site of manufacture and for determining bio-equivalence.

Various methods and devices for dissolution measurement are well known and described in the art.

The US Food and Drug Administration (US FDA) has issued guidelines on the levels of correlation that are more or less desirable in in vitro testing (Guidance for Industry, Extended Release Oral Dosage Forms: Application of In vitro/In vivo Correlations, September 1997). A Level A correlation is one that predicts the entire in vivo time course from the in vitro data. A Level B correlation is one that uses statistical moment analysis. The mean dissolution time is compared either to the mean residence time or to the mean in vivo dissolution time. A Level C correlation establishes a single point relationship between a dissolution parameter and a pharmacokinetic parameter. Level B and Level C correlations do not reflect the complete shape of the plasma concentration-time curve. A Multiple Level C correlation relates in vitro data at several time points to several pharmacokinetic parameters. It is generally considered that if a multiple level C is possible, then Level A correlation should also be possible. Rank order correlations are those where only a qualitative relationship exists between in vitro and in vivo.

A Level A correlation is considered to be the most informative and is recommended by the USFDA wherever possible. Multiple Level C correlations can be as useful as Level A, but a Level A is preferred. Single point Level C correlations are considered useful only in the early stages of formulation development. Level B correlations are the least useful for regulatory purposes. Rank order correlations are not considered useful for regulatory purposes.

Having a high level of correlation, eg Level A, can reduce the amount of in vivo testing necessary for new formulations and can therefore be very valuable to pharmaceutical companies.

The US Pharmcopeia (USP24, pages 1941–1951) describes seven different sets of apparatus for performing dissolution testing. Apparatus 1 and 2 in section <711> (pages 1941–1942) are essentially containers with a suitable stirring device into which is placed a fixed volume of dissolution medium, and the formulation being tested. Samples of the medium are withdrawn at various times and analyzed for dissolved active substance to determine the rate of dissolution. Section <724> (pages 1944–1951) describes various apparatus designed to test dissolution of extended release, delayed release, and transdermal delivery systems. Apparatus 3 (extended release) uses a reciprocating cylinder, Apparatus 4 (extended release) uses a flow-through cell, Apparatus 5 (transdermal) utilizes a paddle over a disk, Apparatus 6 (transdermal) uses a cylinder design, and Apparatus 7 (transdermal) uses a reciprocating holder. Apparatus 1, 2, 3, 5, 6, and 7 use a fixed volume of the dissolution medium. Apparatus 4 uses a continuous flow of dissolution medium. In all cases the volume of dissolution medium used is sufficient to completely dissolve the test substance, frequently known as sink conditions.

For many active substances and dosage forms the principles behind the USP dissolution tests are limiting. These limitations are true for those active substances for which the rate of dissolution is dependent upon the amount of said active substances already dissolved in the release medium. These include, but are not limited to complexes between active substances and ion exchange resins, and poorly soluble active substances. Some combinations of ion exchange resin and active substances form an equilibrium state under fixed volume conditions such that some of the drug remains on the resin, even at infinite time and under sink conditions. This will give rise to incomplete dissolution when using test methods similar to those described in USP24. When an active substances has been dissolved in the gastrointestinal system it is absorbed by the body through the walls of the gastrointestinal system. This results in a decrease in the concentration of the active substance in solution. In the case where the active substance is in equilibrium with the polymeric complex, as described above, this decrease in concentration will displace the equilibrium such that more active substance will be released. As absorption by the body continues, the release of drug from the polymeric complex will be essentially complete. It is therefore clear that the in vitro test as described above, indicating incomplete release, is not predictive of the release in vivo. A similar deficiency will occur with poorly soluble materials when sink conditions do not occur in vivo. The concentration will reach saturation, and the dissolution rate will then depend on the rate of absorption of the active substance by the body. The fixed volume limitation does not apply to the flow-through equipment (Apparatus 4 as described in USP24). In this case the test material is constantly exposed to fresh dissolution medium, where the concentration of active substance is always zero. While this eliminates the equilibrium constraint, and therefore does permit the complete dissolution of such active substances, it still does not simulate the physiological condition where the concentration of active substance is zero only at the start. With formulations controlled by equilibrium or limited solubility it is clear to one skilled in the art that the USP methods cannot be expected to give good IVIVC without further mathematical manipulation of the data. In the current art, Level A IVIVC is obtained by the use of mathematical tools to convert the in vitro data into predicted plasma concentration curves, or similar pharmacokinetic data that reflect the entire time course of the drug in the body. While this is acceptable to the regulatory authorities it is not completely satisfactory because any mathematical model involves basic assumptions, and a major change in a formulation, for example release mechanism or change in solubility, may render those assumptions invalid, requiring the use of a different mathematical model. This limits the predictive power of the IVIVC.

The use of a mathematical model to transform the data is also not ideal because it is not immediately apparent from the raw data obtained in the dissolution test if a change has been significant. It is necessary to transform the data using the model before the effect of the change can be evaluated. The value of a mathematical model is frequently related to the number of independent variables used to adjust the model to fit the in vivo data. As a guideline the USFDA recommends no more than three independent variables.

The conditions that affect dissolution in the gastro-intestinal system are known to vary with position within the gastro-intestinal system. These variations can affect the rate of dissolution of active substances. There have been attempts to simulate these changes in in vitro testing. The main focus has been on the very large pH change between the stomach and upper GI. This change is large enough to have a very serious effect on the solubility of some active substances. For example, diclofenac sodium is essentially insoluble at the low pH of the stomach, but is soluble at the near neutral conditions of the upper GI. In the current art this change of pH has been addressed in two ways. The first has been to change the fluid used in the dissolution test, for example start with gastric fluid and then change to intestinal fluid. The second has been to change the pH gradually by addition of a higher pH solution. Neither of these methods adequately simulates the pH change in vivo because in both methods all the formulation experiences the pH change at the same time, whereas in vivo the pH change is controlled by gastric emptying which causes a gradual transfer of the disintegrated formulation so that different portions of the formulation experience the pH changes at different times. In U.S. Pat. No. 5,807,115 Hu states that it is difficult to move an already disintegrated solid sample. Hu uses this conclusion to justify the gradual change of pH described above.

A method that has been used to solve the problem associated with the USP fixed volume and flow-through methods has been the continuous flow cell in which either the contents of the cell is stirred, or a part of the effluent is recycled to the cell. This allows equilibrium effects to be evaluated.

The equipment described by Huynh-Ngoc and Sirois (J. Pharm Belg, 1976, 31, 589–598; ibid 1977, 32, 67–75) is a continuous flow apparatus. The equipment was designed to facilitate replacement of gastric fluid with intestinal fluid to simulate the transit of the test material through the gastrointestinal system. The authors establish only a rank order VIVC. Takenaka, Kawashima and Lin (J. Pharm Sci, 69, 1388–1392, 1980) describe an apparatus similar in form to that of Huynh-Ngoc and Sirois. The authors made no connection between their data and in vivo performance, although it is clear to one skilled in the art that the limitations will be the same as those for the Huynh-Ngoc and Sirois equipment. Pernarowski, Woo, and Searl (J. Pharm Sci, 57, 1419–1421, 1968) also report the use of a continuous flow method. The authors do make comparison of their results with in vivo performance but it is only a rank order correlation.

The equipment described by Archondikis and Papaioannou (International Journal of Pharmaceutics, 1989, 55, 217–220) is a flow-through cell like the USP Apparatus 4 but returned the fluid removed from the vessel to the fresh fluid reservoir, such that the fluid was continuously recirculated from the reservoir to the flow-through cell and back to the reservoir. This arrangement results in a fixed volume test, the limitations of which have been described above. The equipment described by Miller, Maikner, and Hickey (Am. Chem. Soc, Div. Polym. Chem), 33, 82–83, 1992) is of the flow through type. It has the same limitations regarding IVIVC as does the USP Apparatus 4 described above.

In U.S. Pat. No. 4,335,438 Smolen describes a combination of a flow-through cell with recycle and a mathematical model. The mathematical model is used in conjunction with varying the test parameters to optimize said parameters to give a predicted in vivo plasma curve from the in vitro data. pH change is possible, but it is the same method as used by Hu, and suffers the same limitations. The number of independent variables used is very high. There are four basic variables, flow rate, amount of recycle, pH, and stirring rate. In addition, it is necessary to vary these with time so that the number of possible combinations of variables is essentially infinite. The results obtained using the invention potentially represent a Level A correlation, but based on USFDA guidelines the number of independent variables is too great and so this is not an acceptable model for establishing IVIVC. It is also clear to one skilled in the art that it is possible with this invention to create test parameters that are not physiologically relevant. Regulatory agencies and the USP guidelines strongly recommend that dissolution conditions be physiologically relevant.

In all of the flow-through systems described above only one cell is used per test. There are multiple cell systems available commercially, but these have multiple cells in parallel so that each cell is independent of the other and hence they are a plurality of single cell systems.

Dissolution testing provides a better understanding of the amount of a pharmaceutically active compound available at a particular absorption site at various times. In addition, establishing a relationship between dosage form and availability of a pharmaceutically active compounds at certain absorption sites and systemic blood levels of such active compound aids in the development of specialized delivery techniques.

Dissolution technology that allows determination of IVIVC for pharmaceutically active compounds that exist in complexes wherein the active substance is bound to a solid or other particulate material and exists in a state of equilibrium with the surrounding medium has not yet been developed. Previous techniques for correlating in vitro and in vivo dissolution data have been limited to accounting for such factors as interactions with salts, enzymes, the ionic strength and pH of the medium and temperature. Discrepancies between in vitro and in vivo values of dissolution and absorption have previously been corrected for by transformation of data such as by applying intestinal weighting functions, which transformations may not allow for physiological interpretation.

Thus, there is a need for an integrated assessment of in vitro dissolution of a pharmaceutical formulation and absorption of an active compound from such formulation. Previously these parameters have been considered separately. With the development of more advanced dosage forms, especially for formulations that provide a delayed release of compound, better predictive models are necessary.

Also, there is need for an in vitro dissolution test that takes into account the absorption of the active substance by the body and the presence of dissolved active substance during the dissolution.

Further, there is also a need for an in vitro dissolution test that is able to demonstrate Level A IVIVC without the need for mathematical models to transform the in vitro data. Additionally, there is also a need for an in vitro test that gives data directly comparable with in vivo data without the need for mathematical models to transform the in vitro data.

Finally, there is also need for an in vitro test that can be used with different dosage forms of the same active ingredient that gives Level A IVIVC for other dosage forms without the need for different test conditions for each dosage form.

Surprisingly, Applicant has invented an apparatus and a test method that satisfies all these needs.

The following terms have the following meanings herein:

The terms "medium", "media", or "release medium" as used herein, means the liquid medium into which the active substance is being released. Examples of release media can be water, simulated intestinal fluid, simulated gastric fluid, simulated saliva, or the authentic physiological versions of these fluids, water, and various buffer solutions.

The term "residence time" as used herein, is a well known engineering concept applied to continuous flow systems, and is calculated by mathematically dividing the volume of liquid in a vessel by the flow rate into an out of the vessel such that the volume of liquid remains constant. For example, a flow rate of 5 ml/min into and out of a vessel containing 10 ml of liquid has a residence time of 2 minutes.

The term "resinate" as used herein, means the product derived from forming a complex between an ion exchange resin and an ionizable organic compound.

The term "dosage form," "sample," "composition," "agent," "compound", or "substance" as used herein, means a chemical, a material, a composition, a blend, or a mixture of materials or components that will at least partially dissolve within a release medium to release an active agent. The terms characteristics, parameters, and specifications may be used interchangeably herein and are intended to refer to some property, ingredient, quantity, quality, etc. of a composition or dosage form.

The term "$C_{max}$" as used herein, means the maximum concentration observed in the blood plasma concentration vs time curve for in vivo data, or the cell effluent concentration vs time curve for in vitro data.

The term "$t_{max}$" as used herein, means the time taken to reach $C_{max}$ after the administration of the drug, either in vivo, or in vitro.

The term "$t_{10}$" as used herein, means the time taken after the occurrence of $C_{max}$ for the concentration to fall to 10% of the value of $C_{max}$.

The term "gastric chamber" as used herein, refers to the first of three chambers of the current invention, the design and function of which is described hereinbelow.

The term "intestinal chamber" as used herein, refers to the second of three chambers of the current invention, the design and function of which is described hereinbelow.

The term "circulatory chamber" as used herein, refers to the third of three chambers of the current invention, the design and function of which is described hereinbelow.

The terms 'release profile' and 'dissolution profile' as used herein, mean the change in concentration with time of the substance being tested.

STATEMENT OF THE INVENTION

The present invention relates to an apparatus for conducting dissolution tests comprising:
a) two or more chambers connected in series;
b) a supply of one or more media that can be continuously passed into said chambers;
c) a means of analyzing the effluent from said chambers for substances of interest in the test;
d) a means of controlling the temperature of the medium in said chambers
wherein said first chamber is capable of transferring solid particles to said second chamber;
wherein said second chamber is capable of retaining solid;
wherein said chambers have a means of adding test materials;
wherein said chambers have a means of mixing the sample and medium;
wherein said means of analyzing the effluent can be carried out at multiple times during the operation of the test equipment.

The present invention further relates to a dissolution test method for use with said apparatus, comprising the steps:
a) passing one or more media through the chambers;
b) adding the test sample to the first of said chambers;
c) passing medium through said chambers such that any undissolved portion of the test sample is transferred from the first chamber into the second chamber;
d) passing medium through said chambers such that any undissolved portion of the test sample remains in the second chamber;
e) maintaining the temperature of the medium in said chambers at the desired temperature for the duration of the test;
f) analyzing the effluent from said chambers to determine the concentration of substance dissolved from the test sample, wherein the data obtained from said test correlates with that obtained from in vivo plasma concentrations at Level A, as defined by the USFDA, without the use of a mathematical model.

Said correlation is achieved by manipulation of test method variables including the number of said chambers, number of media, volume of release medium in each of said chambers, flow rate of release medium to each of said chambers, amount of the sample being tested, pH of the media, composition of the media, and temperature.

Finally, the present invention relates to an algorithm for use in optimizing the operational variables for use with said apparatus comprising the steps:
(a) selecting values of residence times for the flow through cells;
(b) predicting the dissolution profile using said algorithm and said residence times;
(c) comparing the predicted results from step (b) with in vivo dissolution data;
(d) estimating improved values of the residence times based on the comparison made in step (c);
(e) repeating steps (a)–(d) until the comparison in step (c) meet acceptance criteria.

DETAILED DESCRIPTION OF THE INVENTION

The present invention relates to an apparatus for conducting dissolution tests comprising:
a) two or more chambers connected in series;
b) a supply of one or more media that can be continuously passed into said chambers;
c) a means of analyzing the effluent from said chambers for substances of interest in the test;
d) a means of controlling the temperature of the medium in said chambers
wherein said first chamber is capable of transferring solid particles to said second chamber;
wherein said second chamber is capable of retaining solid;
wherein said chambers have a means of adding test materials;
wherein said chambers have a means of mixing the sample and medium;
wherein said means of analyzing the effluent can be carried out at multiple times during the operation of the test equipment.

The present invention further relates to a dissolution test method for use with said apparatus, comprising the steps:
a) passing one or more media through the chambers;
b) adding the test sample to the first of said chambers;
c) passing medium through said chambers such that any undissolved portion of the test sample is transferred from the first chamber into the second chamber;
d) passing medium through said chambers such that any undissolved portion of the test sample remains in the second chamber;
e) maintaining the temperature of the medium in said chambers at the desired temperature for the duration of the test;
f) analyzing the effluent from said chambers to determine the concentration of substance dissolved from the test sample, wherein the data obtained from said test correlates with that obtained from in vivo plasma concentrations at Level A, as defined by the USFDA, without the use of a mathematical model.

Said correlation is achieved by manipulation of test method variables including the number of said chambers, number of media, volume of release medium in each of said chambers, flow rate of release medium to each of said chambers, amount of the sample being tested, pH of the media, composition of the media, and temperature.

Finally, the present invention relates to an algorithm for use in optimizing the operational variables for use with said apparatus comprising the steps:
(a) selecting values of residence times for the flow through cells;
(b) predicting the dissolution profile using said algorithm and said residence times;
(c) comparing the predicted results from step (b) with in vivo dissolution data;
(d) estimating improved values of the residence times based on the comparison made in step (c);
(e) repeating steps (a)–(d) until the comparison in step (c) meet acceptance criteria.

Specifically, the invention relates to an apparatus for assessing simulated biological dissolution of a pharmaceutical composition and absorption of a pharmaceutically active compound thereof comprising:
a) a first chamber, herein called the gastric chamber, capable of containing a pharmaceutical composition within a medium; wherein the gastric chamber comprises:
   i) a housing;
   ii) a mixer;
   iii) a first inlet and a first outlet provided on the housing for the supply of a first medium to the housing and outflow of medium from the housing; wherein the said first outlet allows small particles of undissolved solid to exit the chamber along with the medium;
   iv) a second outlet provided on the housing for outflow of medium from the housing;
   v) a second inlet, herein called the sample port, provided on the housing for the addition of test material;
   vi) a filtration device capable of retaining undissolved pharmaceutical composition within the gastric chamber, which is permeable to medium and is positioned between the inside of the housing and said second outlet of the medium, such that the medium flowing out of said second inlet is essentially free of solid particles;
   vii) a flow controller of said first medium into the gastric chamber;
b) a medium analysis device in fluid communication with the gastric chamber for determining the dissolution profile of the pharmaceutical composition; whereby the appearance of the pharmaceutically active compound in the medium flowing out of the intestinal chamber is analyzed to determine dissolution of the compound;
c) a flow controller provided to shunt the medium flowing out of the said second outlet of the gastric chamber, to the inlet of the gastric chamber;
d) a second chamber, herein called the intestinal chamber, in fluid communication with the gastric chamber wherein the intestinal chamber comprises:
   i) a housing;
   ii) a mixer;
   iii) a first inlet and an outlet provided on the housing for the supply of medium to the housing and outflow of medium from the housing;
   iv) a second inlet provided on the housing for the supply of a second medium to the housing;
   v) a filtration device capable of retaining undissolved pharmaceutical composition within the intestinal chamber which is permeable to medium and is positioned between the inside of the housing and outlet of the medium, such that the medium flowing out of said outlet is essentially free of solid particles;
   vi) a medium analysis sensor for analyzing the medium;
e) a medium analysis device in fluid communication with the intestinal chamber for determining the dissolution profile of the pharmaceutical composition; whereby the appearance of the pharmaceutically active compound in the medium flowing out of the intestinal chamber is analyzed to determine dissolution of the compound;
f) a mixing device between the gastric chamber and the intestinal chamber, whereby the medium from the gastric chamber is mixed with a third medium, and the said mixture flows into the intestinal chamber via said first inlet of the intestinal chamber;
g) a flow controller of said second medium into the intestinal chamber; wherein the flow rate of the second medium is adjusted based on the signal from the medium analysis sensor as described in (d)(vi) hereinabove;
h) a flow controller of said third medium into the mixing device;
j) a third chamber, herein called the circulatory chamber, in fluid communication with the intestinal chamber wherein the circulatory chamber comprises:

i) a housing;
ii) a mixer;
iii) a first inlet and an outlet provided on the housing for the supply of medium to the housing and outflow of medium from the housing; whereby the said supply of medium is the same as that flowing out of the intestinal chamber;
iv) a second inlet provided on the housing for the supply of a fourth medium to the housing;
v) a flow controller of said fourth medium into the circulatory chamber;
k) a medium analysis device in fluid communication with the circulatory chamber for determining the dissolution profile of the pharmaceutical composition; whereby the appearance of the pharmaceutically active compound in the medium flowing out of the intestinal chamber is analyzed to determine dissolution of the compound;
l) heating and insulating devices provided to control the temperature of the media in the chambers.

Figure 1:
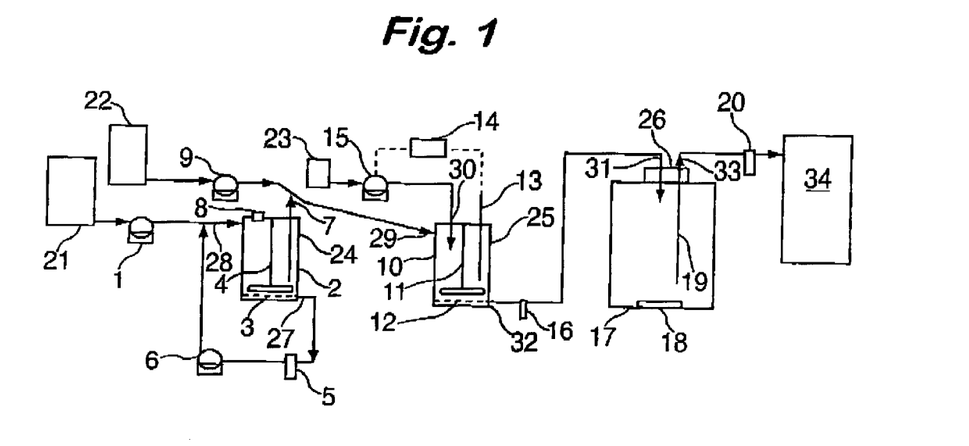
FIG. 1 is a schematic representation of one embodiment of the invention comprising three cells.

FIG. 1 schematically illustrates one embodiment of the dissolution apparatus of the present invention. A reservoir (21), a pump (1), and a filtration cell (2) are connected such that the liquid contents of the reservoir (21) is transferred into the filtration cell (2) via the pump (1). The filtration cell (2) is equipped with a tight fitting lid (24), a filtration membrane (3), a stirrer (4), an inlet (28), an outlet positioned to allow removal of filtered liquid (27), a sample addition port (8), and a dip-tube and Tee assembly (7). The outlet (27) is connected to a flow-thru uv cell (5) and pump (6), such that the filtrate is pumped through the uv cell (5) and returned to the inlet of the filtration cell (2). One branch of the dip-tube and Tee assembly (7) comprises a dip-tube to allow removal of liquid and small particle size solid from the filtration cell (2). The second branch of the dip tube and Tee assembly is connected to the outlet of a pump (9). The third branch of the dip-tube and Tee assembly (7) is connected to the inlet (29) of a second filtration cell (10). A reservoir (22) is connected to the pump (9) such that the liquid from the reservoir (22) is fed into the second branch of the dip-tube and Tee assembly (7). The filtration cell (10) is equipped with a tight fitting lid (25), a pH sensor (13), a stirrer (11), a filtration membrane (12), two inlets (29 and 30), and an outlet positioned to allow removal of filtered liquid (32). A reservoir (23) is connected to a pump (15) and to one of the inlets (30) of the filtration cell (10), such that liquid from the reservoir (23) is transferred into the filtration cell (10). The outlet (32) is connected to a flow-thru uv cell (16). The outlet of the uv cell (16) is connected to the inlet (31) of the cell (17). The pH sensor (13) is electrically connected to a pH controller (14). The power supply to pump (15) is connected to the output relay of the pH controller (14) such that the pump (15) is turned on when the pH as measured by the pH sensor (13) is below a target value, and is turned off when said pH is above a target value.

The cell (17) is equipped with a tight fitting lid (26), a stirrer (18), a dip-tube (19), and an outlet (33). The outlet is connected to the inlet of a flow-thru uv cell (20). The outlet from the uv cell (20) is directed to waste or any suitable reservoir (34). In this embodiment, the filtration cell (2) and immediately associated equipment represents the gastric chamber; the filtration cell (10) and immediately associated equipment represents the intestinal chamber; the cell (17) and immediately associated equipment represents the circulatory chamber.

Each of the flow-thru uv cells (5, 16, and 20) is placed in a suitable uv spectrophotometer capable of measuring the absorbance of the cell contents at the desired wavelength.

Figure 2:
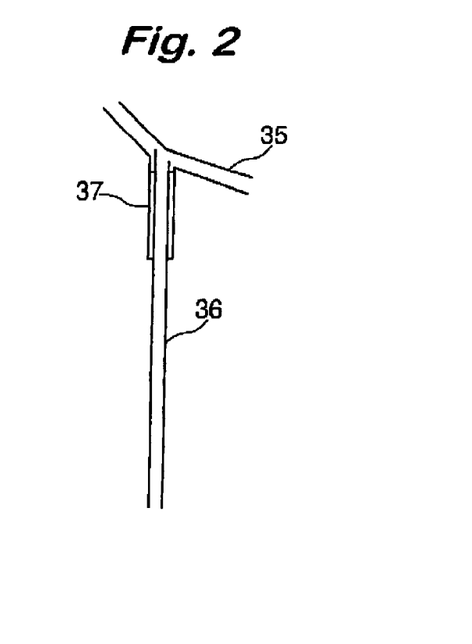
FIG. 2 is a schematic representation of the dip-tube and Tee assembly.

FIG. 2 schematically illustrates one embodiment of the mixing device herein called a dip-tube and Tee assembly. Said dip-tube and Tee assembly (7) comprises a Y-shaped connector (35), a length of tubing (36), and a sealant (37). The tubing (36) is inserted into one of the branches of the connector (35) together with a sealant to prevent leakage of liquid and to hold said tubing in place during operation. The length of the tubing is adjusted so that it's lower end is below the surface of the liquid when the equipment is operating. This arrangement allows the transfer of small particles between the gastric and intestinal chambers without clogging the tubing. Large particles are not transferred by this arrangement because they are too large to enter the dip tube or because the flow velocity of the medium in the said dip tube is insufficient to carry the said large particles up said dip tube.

When control of the temperature is required any or all of the three cells can be immersed in a suitable heating bath, which are very well known in the industry. In one embodiment, reservoir (21) is filled with simulated gastric fluid, reservoir (22) is filled with simulated intestinal fluid, and reservoir (23) is filled with 0.8M aqueous sodium hydroxide solution. To start a test, the pumps are operated to fill each of the chambers to the desired volumes, and then run for sufficient time to establish that the flow rate from each pump is as desired and the pH of cell (10) is maintained within the target range. The uv cells are checked to make sure that they contain no air bubbles. In one embodiment the sample addition port (8) is a hole with a rubber stopper. For said embodiment the pumps are momentarily stopped, the stopper is removed, and the sample to be tested is added to the filtration cell (2). The stopper is immediately replaced and the pumps restarted. Exposure to the fluid in the gastric chamber causes the sample to be partially or completely disintegrated, and/or dispersed, and/or dissolved. The dissolved portion exits the gastric chamber via the tube (36) together with small particles of undissolved drug and/or excipient. Dissolved drug and/or dissolved excipient also exits the gastric chamber through the outlet (27). The filter membrane (3) prevents undissolved particles from exiting through the outlet (27). The liquid that exits though outlet (27) passes through the uv cell (5), where it's uv absorbance at any desired wavelength is continuously monitored. Said liquid is continuously returned to the gastric chamber via the inlet (28). The material exiting via the tube (36) enters the Tee (35) where it mixes with simulated intestinal fluid from the pump (9). This mixture then enters the intestinal chamber via the inlet (29).

In the intestinal chamber the incoming mixture is mixed with the contents of said chamber together with sodium hydroxide solution entering from pump (15). Because the sodium hydroxide flow is controlled by the pH of the contents of the cell (10) the result is that the acid present in the gastric fluid portion of the incoming mixture is neutralized. In the intestinal chamber the undissolved portion of the incoming mixture has further opportunity to dissolve. Dissolved drug and/or dissolved excipient exits the intestinal chamber through the outlet (32). The filter membrane (12) prevents any undissolved drug and/or undissolved excipient from exiting said chamber. The liquid that exits though outlet (32) passes through the uv cell (16), where it's uv absorbance at any desired wavelength is continuously monitored. The liquid exiting the uv cell (16) then enters the circulatory chamber via the inlet (31).

In the circulatory chamber the incoming medium is mixed with the medium already present in said chamber. The resulting mixture continuously exits the chamber via the dip-tube (19) and outlet (33). The liquid that exits though outlet (33) passes through the uv cell (20), where it's uv absorbance at any desired wavelength is continuously monitored.

The data collected from the spectrophotometer can be used to calculate the instantaneous concentration of the active substance. The data can be used to characterize the release rate and the total amount of active substance released. Measuring the concentration of active substance in the effluent collected in the collection reservoir (34) permits the calculation of the total amount of active substance released.

While the embodiment of the invention described above and illustrated by the examples uses constant composition of release fluids within each test, it is clear that the compositions can be changed with time, for example, as taught by Waaler (J Pharm Sci, 82, 764–766, 1993), to simulate changing conditions within the body. Test method variables are composition of release media, residence time in each of the three chambers, amount of the sample being tested, and temperature. By adjusting these variables it is possible to obtain a release rate profile that matches the plasma concentration profile observed in vivo. When practiced in the pharmaceutical industry the preferred temperature is 37° C., and the preferred composition of the release media are simulated gastric and simulated intestinal fluids, recommended compositions for both of which can be found in the most recent edition of the US Pharmacopeia. It is also clear to one skilled in the art that other additives, such as enzymes, bile acids, and surfactants, can be included where their need is demonstrated. The USFDA recommends that dissolution conditions be physiologically relevant. However, it is clear to one skilled in the art that the present invention can be adapted for conditions that are not physiologically relevant. Such conditions may be desirable when considerations such as speed of operation, unusual solubility, or non conventional dosage forms are taken into account. For example, applicant has determined in some cases that by proportionally reducing residence times, the time scale of the test can be considerably shortened without loss of useful information.

The invention can be used to test many different types of formulation. These can include, but are not restricted to, tablets, powders, pills, syrups, fast-melt tablets, hard capsules and soft capsules.

The medium analysis device includes, but is not limited to, any detector known in the art that generates physical and/or chemical data of a pharmaceutical or active test agent, e.g., the use of a UV spectrophotometer as the method of analysis. In a preferred embodiment, the detector is capable of acquiring data characteristic of a particular agent by method selected from the group consisting of ultraviolet radiation, infrared radiation, nuclear magnetic resonance, Ramen spectroscopy, electrochemical, biosensors, refractometry, optical activity, and combinations thereof. Any in-line detector known in the art that is applicable to the active substance and release medium can be also be used. Preferably, the medium dissolution analysis device is a detector that has a sensor communicatively attached thereto. In the preferred embodiment, there is at least one medium dissolution analysis device per dissolution chamber. For example, for each sample to be analyzed there is a corresponding medium dissolution analysis device capable of continuously generating physical and/or chemical data characteristic of the agent to be analyzed.

The medium analysis device preferably includes a detector operatively associated with the dissolution medium for at least the time period required for the dosage form to release the maximum releasable quantity of therapeutically active agent and a data processor for continually processing the generated data for at least the time period required for the dosage form to release the maximum releasable quantity of therapeutically active agent to obtain a dissolution profile of the dosage form. The data processor may be any device capable of continuously processing the data generated by the detector. In a preferred embodiment, the data processor is a computer. The data generated by the detector is preferably stored and/or analyzed by the computer. In a particularly preferred embodiment, the data collector is a computer that has data processing software. The data is preferably continuously processed by the software as it is received from the detector. In the preferred embodiment of the present invention, the detector measures the concentration of the therapeutically active agent in the media surrounding the dosage form such as in simulated gastric or intestinal fluid. By measuring the concentration of the agent in the surrounding media, the amount of agent released from the dosage form can be calculated. The invention can also be used by removing samples from the chambers directly or from the effluent discharge of the chambers instead of, or in addition to in-line analysis. In such an embodiment the analytical methods can be any method known in the art, including but not limited to, Gas chromatography, liquid chromatography, high performance liquid chromatography (HPLC), colorimetry, uv spectroscopy, IR spectroscopy, Raman spectroscopy, near IR spectroscopy, bio-sensors, electrochemical methods, mass spectroscopy, and nuclear magnetic spectroscopy.

In the most preferred embodiment the medium analysis is performed in-line using uv spectroscopy.

It is clear to one skilled in the art that any combination of the medium analysis devices can be used as appropriate for the data required. In another embodiment the absorption of active substance in the stomach can be simulated by not returning to the gastric chamber, all or part of the medium exiting the gastric chamber via the second outlet. The flow rate of said medium can be adjusted so that the removal rate corresponds to the in vivo gastric absorption.

The filtration cells (2) and (10) can be of any design that provides the requirements of agitation, desired volume, filtration speed, filtration efficiency, and compatibility with the active substance and the release media. The preferred filtration cells are continuous, stirred, filtration cells, such as the Amicon stirred ultrafiltration cell models 8003, 8010, 8050, 8200, and 8400 available from Millipore Corporation. The lids and height of these cells can be modified to fulfill the requirements as described hereinabove.

The third cell (17) can be of any design that provides the requirements of agitation, desired volume, and compatibility with the active substance and the release media. The pumps useful in the practice of the present invention can be any pump capable of attaining the desired flow rate and maintaining said flow rate constant throughout the test. These include but are not limited to, general purpose positive displacement pumps, peristaltic pumps, diaphragm pumps, HPLC quality positive displacement pumps, and centrifugal pumps. Preferred pumps useful in the invention are peristaltic pumps, diaphragm pumps, and HPLC quality positive displacement pumps. Most preferred are peristaltic pumps and HPLC quality positive displacement pumps.

Heating devices useful in the practice of the present invention can be any of those known in the art that give sufficiently uniform and accurate temperature control. The preferred heating device will be able to control the temperature to within +/−2° C. of the desired temperature. The more preferred heating device will be able to control the temperature to within +/−1° C. of the desired temperature. The most preferred heating device will be able to control the temperature in conformity with the most current recommendations in the US Pharmacopeia and like sources.

The tubing used in the dip-tube and Tee assembly can be any tubing compatible with the release medium and the test sample. The length of said tubing is adjusted such that the lower end is below the surface of the liquid in the filtration cell (2). The cross-sectional diameter of the tubing is selected so that small particles are carried up the tubing by the flow of the release medium and so that particles do not clog the tubing. In practice, the inventors have determined that tubing with an internal diameter of 0.5 to 3.0 mm fulfills these requirements for flow rates to the cell (2) in the range 0.5 to 2.5 m/min. For other flow rates other internal diameters may be needed. It is clear to one skilled in the art that suitable internal diameters for the said tube can be selected by trial and error, or by calculation using suitable hydrodynamic considerations.

The medium analysis sensor and controller used with the intestinal chamber can be any combination of sensor and controller that measures and permits control of physical characteristics such as, but not limited to, pH, osmolarity, conductivity, and concentration of specific ions.

The preferred medium analysis sensor and controller are any pH sensor and pH controller available in the art that permit the control of the pH in the intestinal chamber to within the target range. The most preferred medium analysis sensor and controller are any pH sensor and pH controller available in the art that has an accuracy of +/−0.02 pH units.

In the preferred embodiment the pH in the second cell (10) is controlled to the same value as that of the simulated intestinal fluid. It is clear to one skilled in the art that the pH in the said cell can be any value achievable by addition of either an acid or a base through the delivery system defined by the reservoir (23), the pump (15), and the inlet (30), and is not limited to the pH of the fluid in the reservoir (22).

The solution used to adjust the pH of the second cell can be acidic or basic. The preferred concentration of acid or base in said solution is one that requires a flow rate of said solution to be not more than 10% of the total flow of the other release media. The most preferred concentration of acid or base in said solution is one that requires a flow rate of said solution to be not more than 2% of the total flow of the other release media.

The number of cells used in the equipment can be varied depending on the information required. Three cells, as described in one embodiment above, is the preferred number when correlation with blood plasma concentration data is required. When drug absorption rate data is required it is only necessary to operate the combination of gastric and intestinal chambers. A further possibility is to add a buccal dissolution cell before the gastric chamber such that the effluent from the buccal dissolution chamber enters an inlet in the gastric chamber. Said addition can be used for either drug absorption or blood plasma concentration data.

Filter membranes useful in the practice of this invention can be any of the commercially available filter membranes that are compatible with the release media. Preferred filter membranes have a nominal particle size cut-off of not more than 10 microns. The more preferred filters have a nominal particle size cut-off of 0.25–5 microns. The most preferred filter membranes have a nominal particle size cut-off of 1–3 microns.

The volumes of the three chambers and the flow rates of the various media are calculated based on the desired residence times for each of the chambers. This calculation is well known in the art and is described hereinabove.

Residence times in each of the chambers useful in the practice of this invention can be any value required to give Level A IVIVC. The preferred residence times are those that have physiological relevance. The applicant has determined by experimentation that the following ranges of residence times are useful: gastric chamber, 5–60 minutes; intestinal chamber, 1–90 minutes; circulatory chamber, greater than 30 minutes.

It is known to those skilled in the art that the safe and effective use of flow controlling devices such as pressure feed systems and pumps requires the inclusion of various other mechanical, electrical and electronic equipment. Said equipment includes, but is not limited to, pressure relief valves, check valves, pressure relief piping, pressure control systems, surge suppressors, surge tanks, de-aerators, electronic flow control systems, proportional control systems, pressure gauges, and flow gauges.

Further, the invention relates to a dissolution test method for use with the apparatus described hereinabove, comprising the steps of:

a) passing one or more media through the chambers;
b) adding the test sample to the first of said chambers;
c) passing medium through said chambers such that any undissolved portion of the test sample is transferred from the first chamber into the second chamber;
d) passing medium through said chambers such that any undissolved portion of the test sample remains in the second chamber;
e) maintaining the temperature of the medium in said chambers at the desired temperature for the duration of the test;
f) analyzing the effluent from said chambers to determine the concentration of substance dissolved from the test sample, wherein the data obtained from said test correlates with that obtained from in vivo plasma concentrations at Level A, as defined by the USFDA, without the use of a mathematical model.

Said correlation in data is achieved by manipulation of test method variables including the number of said chambers, number of media, volume of release medium in each of said chambers, flow rate of release medium to each of said chambers, amount of the sample being tested, pH of the media, composition of the media, and temperature.

Finally, the present invention relates to a method for predicting the in vitro dissolution profile of a pharmaceutically active compound comprising using an algorithm to reduce the time required to optimize dissolution test conditions.

As described hereinabove, the method of the present invention typically operates on a time-scale that is the same as the time-scale of the in vivo absorption and metabolism of the active substances being tested. This can give rise to tests that take up to 24 hours. While this is not a major problem once the test conditions are established, it does present a problem for the development of the optimal residence times because there is a wide range of possible values for each of the residence times, and it may take many iterations of the test to determine reasonable conditions, and then several more to determine the optimal conditions. Consequently, it is expected that test method development times will be in the range of 2–5 weeks. The use of the algorithm reduces test method development time.

Specifically, the algorithm calculates the composition of the fluid in each of the flow-through cells of the dissolution apparatus of the present invention. The calculation is done in a sequential, stepwise manner over many iterations. Each iteration covers a small period of time. The combination of these iterations results in a complete dissolution profile.

Figure 3:
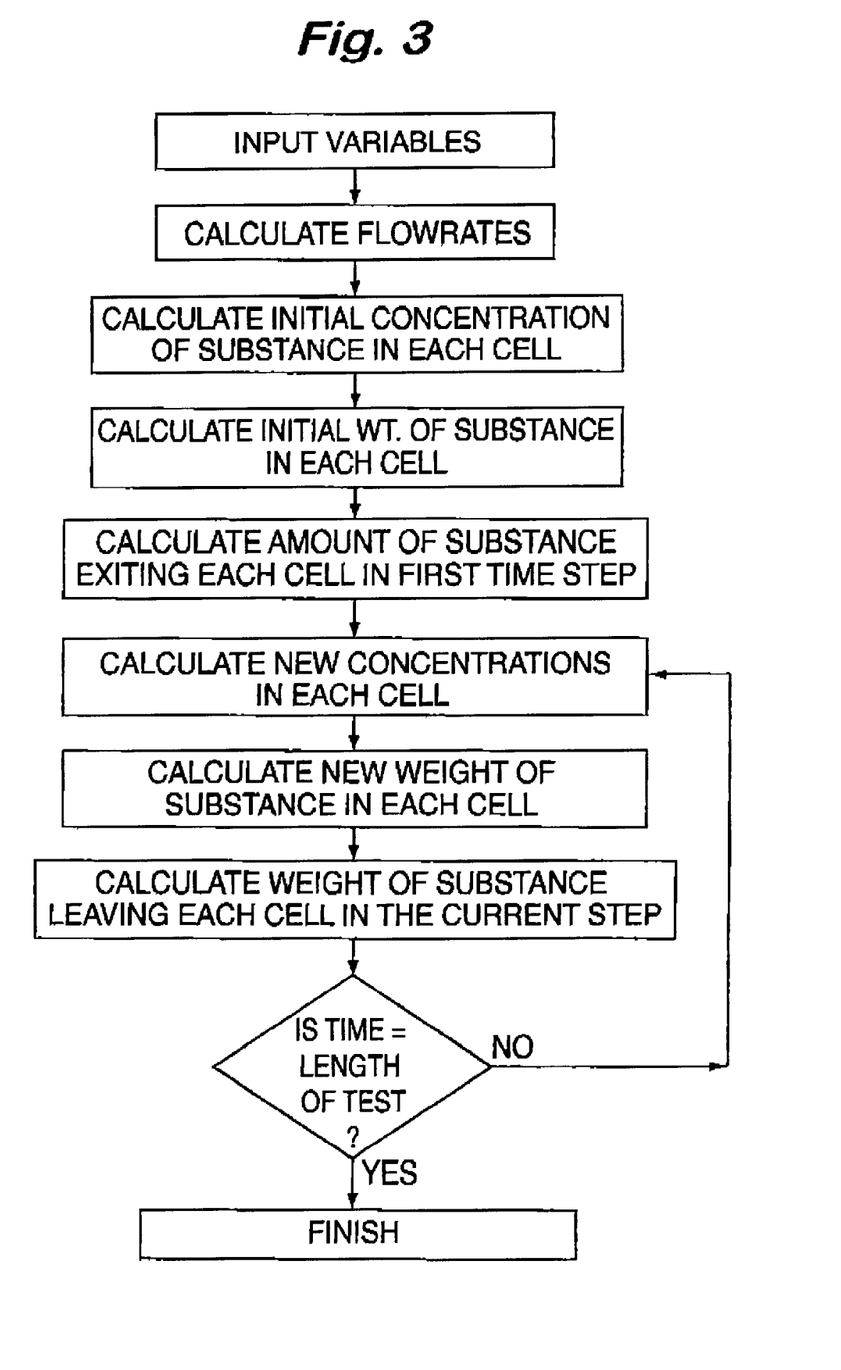
FIG. 3 is a schematic illustration of the general architecture of the algorithm.

Referring now to FIG. 3, which depicts the general architecture of the algorithm, the first step is to enter the initial input variables as specified below. The algorithm then calculates the various flow rates, initial concentrations and the weight of substance in each cell, based on the input variables. Once values for the above mentioned variables have been calculated the initial state of the system has been defined. The algorithm then considers the first step, or iteration, by calculating the amount of substance that exits each of the cells in said first step. The amount that exits the first cell is considered to be equal to the amount of substance entering the second cell. The amount of substance exited the second cell is considered to be equal to the amount of substance entering the third cell. Using these amounts, the algorithm then recalculates the new concentrations and weight of substance in each cell. Once values for the above mentioned variables have been calculated, the state of the system at the end of the first step has been defined. The algorithm then moves to the second step, and repeats the above calculations to generate a third step, and a fourth step, and so on. The algorithm continues until the total amount of time considered is equal to the total length of the test defined in the initial input variables.

The algorithm uses the following variables to calculate the profile:

| Step # | sequential number of the iteration currently being calculated |
|---|---|
| C1 Conc | concentration of the substance in the fluid contained in the first cell |
| C2 Conc | concentration of the substance in the fluid contained in the second cell |
| C3 Conc | concentration of the substance in the fluid contained in the third cell |
| Time | time since the start of the test |
| C1 wt | weight of the substance present in the first cell |
| C2 wt | weight of the substance present in the second cell |
| C3 wt | weight of the substance present in the third cell |
| C1 out | weight of the substance that exits the first cell during one step of the calculation |
| C2 out | weight of the substance that exits the first cell during one step of the calculation |
| C3 out | weight of the substance that exits the first cell during one step of the calculation |
| C1 vol | volume of fluid in the first cell |
| C2 vol | volume of fluid in the second cell |
| C3 vol | volume of fluid in the third cell |
| C1 Res | residence time in the first cell |
| C2 Res | residence time in the second cell |
| C2 Res | residence time in the third cell |
| F1 | Flow rate of release fluid 1 to the first cell |
| F2 | Flow rate of release fluid 2 to the second cell |
| F3 | Flow rate of release fluid 3 to the third cell |
| F(1 + 2) | flow rate exiting the second cell |
| F(1 + 2 + 3) | flow rate exiting the third cell |
| Length of test | total time for which the test is run |
| Steps total | The total number of iterations used for the completion of the algorithm |
| Timestep | The length of time used for each iteration. Time step = Length of test/steps total |
| W | weight of the substance originally added to the first cell |
| Disint | A correction factor used to account for the disintegration time of real dosage forms. |

One skilled in the art will appreciate that various units for each parameter can be used with the algorithm as long as they are consistent. In one embodiment, the units are as follows:

| Volume | liters (l) |
|---|---|
| Time | minutes (mins) |
| Flow rate | liters/minute (1/min) |
| Weight | milligrams (mg) |
| Concentration | milligrams/liter (mg/l) |

The algorithm requires the input of values for the following variables:
Length of Test
Steps Total
W
C1 vol
C2 vol
C3 vol
C1 res
C2 res
C3 res The algorithm proceeds as follows:
a. Calculate F1=C1 vol/C1 res
b. Calculate F2=C1 vol/C1 res
c. Calculate F3=C1 vol/C1 res
d. Calculate F(1+2)=F1+F2
e. Calculate F(1+2+3)=F1+F2+F3
f. Set Step #=0
g. Calculate: C1 Conc=W/C1 vol. C2 Conc and C3 Conc are set at zero
h. Calculate: Time=Step #×timestep
i. Calculate C1 wt=C1 vol×C1 conc
j. Calculate C2 wt=C2 vol×C2 conc
k. Calculate C3 wt=C3 vol×C3 conc
l. Calculate C1 out=C1 conc×timestep×F1
m. Calculate C2 out=C2 conc×timestep×F(1+2)
n. Calculate C3 out=C3 conc×timestep×F(1+2+3)
o. Calculate a new value for Step #=Step #+1
p. Calculate a new value of C1 conc=(C1 wt−C1 out)/C1 vol
q. Calculate a new value of C2 conc=(C1 out+C2 wt−C2 out)/C2 vol
r. Calculate a new value of C3 conc=(C2 out+C3 wt−C3 out)/C3 vol
s. Calculate a new value of Time=Step #×timestep
t. Calculate a new value of C1 wt=C1 vol×C1 conc
u. Calculate a new value of C2 wt=C2 vol×C2 conc
v. Calculate a new value of C3 wt=C3 vol×C3 conc
w. Calculate a new value of C1 out=C3 conc×timestep×F1
x. Calculate a new value of C2 out=C2 conc×timestep×F(+2)
y. Calculate a new value of C3 out=C3 conc×timestep×F(+2+3)
z. Repeat calculations o through y until Step #>Step total The output from the algorithm can be represented in a number of different ways. A graph of C1 conc vs time represents the change in concentration of the substance in the first cell. A graph of C2 conc vs time represents the change in concentration of the substance in the second cell. The graph C2 conc vs time is representative of the in vivo absorption profile of a substance. A graph of C3 conc vs time represents the change in concentration of the substance in the third cell. The graph C3 conc vs time is representative of the in vivo blood plasma concentration profile of a substance. The sum of all C1 out from time=0 to any value of time, represents the total amount of the substance that has passed through the first cell at that value of time. A graph of these values calculated for each iteration, plotted against time gives the cumulative dissolution profile for the first cell. The sum of all C2 out from time=0 to any value of time, represents the total amount of the substance that has passed through the second cell at that value of time. A graph of these values calculated for each iteration, plotted against time gives the cumulative dissolution profile for the second cell. The sum of all C3 out from time=0 to any value of time, represents the total amount of the substance that has passed through the third cell at that value of time. A graph of these values calculated for each iteration, plotted against time gives the cumulative dissolution profile for the third cell.

In another embodiment of the invention, the algorithm includes a factor to account for the disintegration time of a real dosage form. The factor, Disint, has the units of time and is incorporated by replacing calculation h above with the following:

Time=Disint+(Step #xtimestep)

Figure 4:
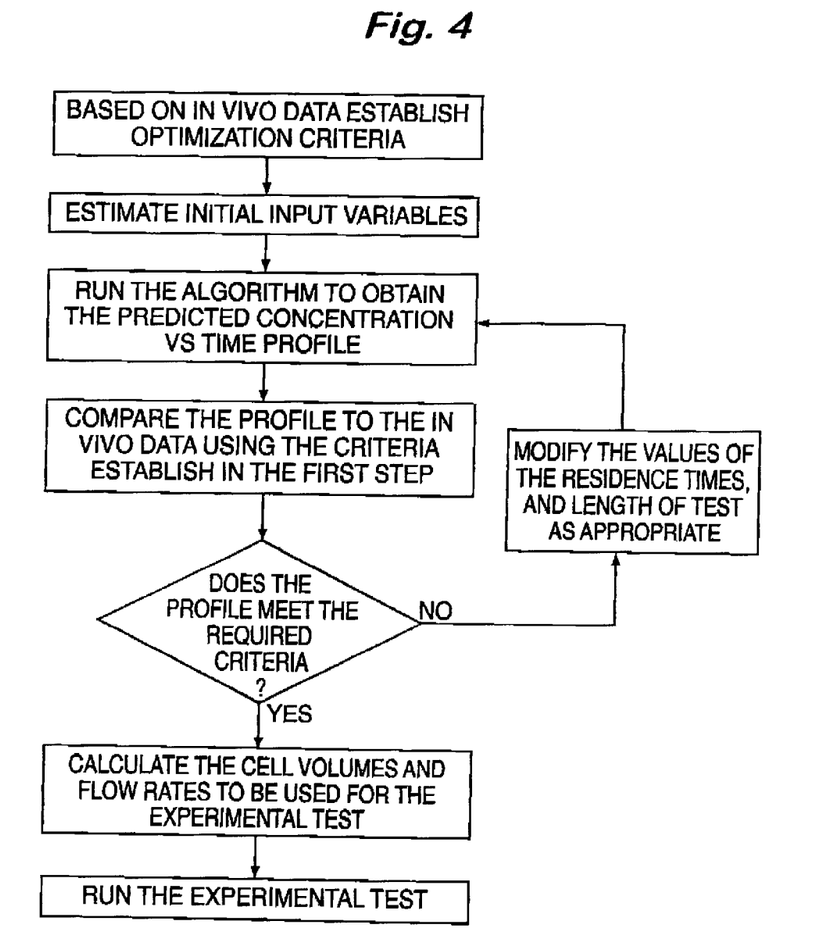
FIG. 4 is a schematic illustration of the architecture of the optimization method.

The general architecture of the method for using the algorithm to optimize conditions for experimental testing is illustrated in FIG. 4.

In one embodiment, the method of use for this algorithm is as follows:

a. Estimate the $t_{max}$ and $t_{10}$ for the in vivo blood plasma concentration profile.

b. Use the algorithm to determine residence times for the three cells that gives values of $t_{max}$ and $t_{10}$ that are closely matched to the in vivo data. At this point in the method the specific values of W, C1 vol, C2 vol, and C3 vol are not critical to the calculation. Changing their values will not change the values of $t_{max}$ and $t_{10}$. To retain physiological relevance suggested ranges for the residence times, C1 Res, C2 Res, and C3 Res are 5 to 60 minutes, 1 to 90 minutes, and >30 minutes respectively.

c. Using the residence times that give the best match for $t_{max}$ and $t_{10}$, calculate flow rates and volumes to obtain said residence times. Flow rates to the first and second chambers should meet the flow rates requirements specified hereinabove. C3 vol should be adjusted so that the additional flow to the third cell is zero, as recommended hereinabove.

In a second embodiment, the method of use for this algorithm is as follows:

a. Use the linear regression coefficient, $R^2$ as the criterion of best fit.

b. Run the algorithm. Compare the results of this run with the in vivo data by mathematically regressing the in vivo time vs concentration data and the algorithm time vs concentration data to obtain a linear regression coefficient, $R^2$.

c. Change one or more values of the residence time to obtain a new data set. Determine the linear correlation coefficient for this data set and the in vivo data.

d. Continue testing different values of residence times to maximize the linear correlation coefficient. Useful ranges for the residence times are described hereinabove.

e. Using the residence times that give the maximum linear correlation coefficient, calculate flow rates and volumes to obtain said residence times.

Flow rates to the first and second chambers should meet the flow rates requirements specified hereinabove. C3 vol should be adjusted so that the additional flow to the third cell is zero, as recommended hereinabove.

It is known to those skilled in the art that there are other approaches to obtaining the optimal residence times for use in the algorithm. These include visual comparison, other statistical methods of comparison, and other specific time/ concentration points, factorial design, evolutionary optimization, and sequential simplex. These can be used to improve the efficiency of the trial and error determination of the optimal residence times.

Although the algorithm can be used by manual calculation, it does not realize its true benefit of speed unless said algorithm is programmed into a computer to perform the calculations. Any suitable programming language or system can be used. In one embodiment, the Applicant has written this algorithm into a computer spreadsheet, where each iteration of the calculation is carried out on one row of the spreadsheet, and other sections of the spreadsheet are used for data input and results output. When the algorithm is operated as a computer spreadsheet the time taken to complete calculations of said algorithm is approximately 1 second. Depending on the optimization approach selected, it is therefore possible to run several sets of conditions in one minute and >100 runs in one hour. This should be compared to the 4 to 24 hours needed to run one test when actually operating the apparatus of the current invention. Thus, as an example, a method development that would require 20 separate tests to identify residence times that give reasonable correlation with in vivo data could be completed in less than one hour using the algorithm. Without the algorithm, the time required would be 2 to 4 weeks. The accuracy of the correlation between the algorithm and the test equipment are demonstrated in the Examples.

The algorithm makes the assumption that all the test substance is dissolved quickly, such that there is no significant amount of undissolved solid in the second cell. The result of this assumption is that when the algorithm is applied to pharmaceutical dosage forms it is only applicable to immediate release dosage forms.

The number of iterations (Steps total) strongly influences the accuracy of the algorithm. Very low values give insufficient resolution between iterations. Very high values will cause the accumulation of calculation errors because values of C1 out, C2 out and C3 out become too small for accurate representation by the computer. Values of Steps total useful in the practice of this invention are from 100 to 20,000. Preferred values are from 1,000 to 10,000. Most preferred values are from 2,000 to 5,000.

The apparatus and its utility in dissolution testing are illustrated by the following non-limiting examples:

EXAMPLE 1

Comparative Example—Single Cell Dissolution Test

Equipment was set up as follows: A continuous, stirred, filtration cell, such as the Amicon stirred ultrafiltration cell model 8050, available from Millipore Corporation, was equipped with a peristaltic pump to feed fluid into the cell at a rate in the range 3–10 ml/min. The filtrate from the cell was passed into a 1 cm path length flow-through quartz uv cell. The uv cell is situated in a suitable uv spectrophotometer, such as the Genesys 2, UV Spectrophotemer available from Spectronic Instruments. The filtration cell was fitted with a 3 micron filter to retain undissolved particles. 60 ml of simulated intestinal fluid pH 7.4 was added to the filtration cell, and then simulated intestinal fluid was fed into it via the pump at a flow rate of 6.5 ml/min. This was continued until the absorbance at 276 nm as measured in the uv cell was constant. 50 mg of diclofenac sodium was then added to the filtration cell. The uv absorbance at 276 nm of the effluent from the cell was recorded through the duration of the test. The concentration was calculated using a suitably determined calibration curve. In Table 1 the data from this experiment is compared with in vivo data reported in U.S. Pat. No. 4,510,128. The flow rate for this example was optimized such that the uv absorbance returned to baseline within approximately the same time (8 hours) as the in vivo data. Note that the correlation coefficient is very low (0.1) and the $t_{max}$ values do not correspond. This demonstrates that a single cell system does not give a concentration time profile that directly matches the in vivo data.

EXAMPLE 2

Three Cell Dissolution Test Using Ibuprofen

The three cell equipment of this invention was operated as follows. The release media were simulated gastric fluid, (as per USP24, without pectin) and simulated intestinal fluid (as per USP24, pH 7.4). The pH in the second cell was controlled at 7.4+/−0.02. The flow rates and volumes were adjusted so that the residence times in the gastric, intestinal, and circulatory chambers were 20, 16, and 168 minutes respectively. The uv absorbance was measured at 265 nm. One 200 mg sugar coated ibuprofen tablet (200 mg Advil®) was used. The data from this experiment is summarized in Table 2 and compared with in vivo data reported in Clin. Drug Invest. Volume 21, pages 73–78, 2001 for the same dosage from. The correlation coefficient for this comparison was 0.993 and the $t_{max}$ values correspond. This example demonstrates that the invention gives excellent correlation with in vivo data.

EXAMPLE 3

Three Cell Dissolution Test Using Diclofenac Sodium

The three cell equipment of this invention was operated as follows. The release media were simulated gastric fluid, (as per USP24, without pectin) and simulated intestinal fluid (as per USP24, pH 7.4). The pH in the second cell was controlled at 7.4+/−0.02. the uv absorbance was measured at 276 nm. The flow rates and volumes were adjusted so that the residence times in the gastric, intestinal, and circulatory chambers were each 35 minutes. 50 mg of diclofenac sodium was added to the first cell. The data from this experiment is summarized in Table 1 and compared with in vivo data reported in U.S. Pat. No. 4,510,128. The correlation coefficient for this comparison was 0.960 and the $t_{max}$ values correspond. This example demonstrates the improvement of the 3-cell system over the single cell system (Example 1).

EXAMPLE 4

Three Cell Dissolution Test Using a Diclofenac Resinate

The conditions of Example 3 were repeated except that a complex of diclofenac and an anion exchange resin (prepared as described in U.S. Pat. No. 4,510,128, Example 1(a)). This formulation gives an extended release of the active ingredient. The amount used was equivalent to 50 mg of diclofenac sodium. The results of this test are given in Table 3 and compared with in vivo data provided in said patent. The correlation coefficient for this comparison is 0.82 and the $t_{max}$ values are very similar. This example demonstrates the predictability of the invention in that test conditions determined in one dosage form, in this case an immediate release formulation, give results with good IVIVC for a different dosage form of the same active ingredient, in this case an extended release formulation.

EXAMPLE 5

Predicted and Actual Results for Ibuprofen

The three cell test equipment was operated with the release medium and at the pH described in Example 2. 200 mg of ibuprofen was used.

The algorithm was used to match the $t_{max}$ and $t_{10}$ for ibuprofen in vivo data (T. Schettler et al, Clin. Drug Invest 21, 73–78, 2001). $t_{max}$ and $t_{10}$ for in vivo data were 70 and 410 minutes respectively. The best fit with the algoritm gave $t_{max}$ and $t_{10}$ values of 70.7 and 410.8 respectively. The resulting residence times for the first, second and third cell were 20, 16, and 168 minutes respectively. F1, F2, F3, C1 vol, C2 vol, and C3 vol were than calculated according to the guidelines described above, getting the following values: F1=0.0025/min; F2=0.0075 l/min; F3=0; C1 vol=0.050 l; C2 vol=0.16 l; C3 vol=2.1.1.

Figure 5:
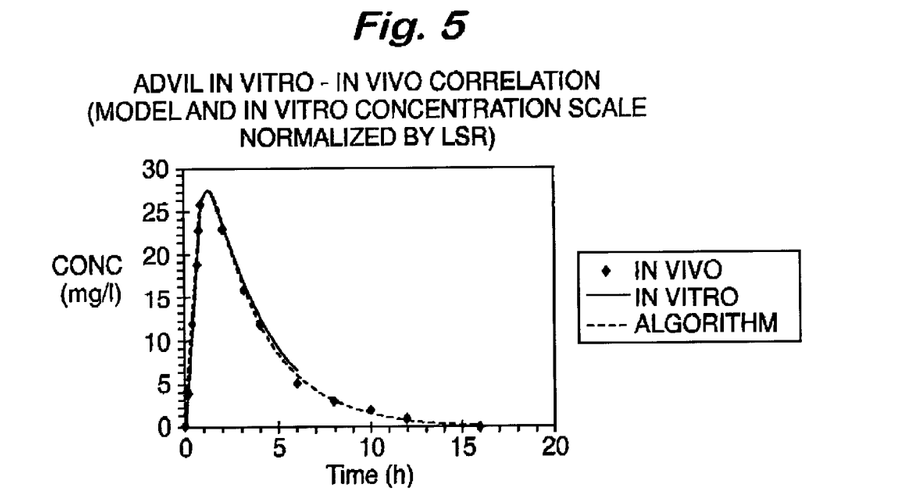
FIG. 5 is a graph showing the comparison of in vivo, predicted in vitro, and in vitro data for ibuprofen (Advil®).

The data from this example is shown in FIG. 5. The data from the algorithm and the in vitro test has been adjusted using a linear scaling factor so that the data can be compared with the in vivo data. The excellent correlation between all three datasets is clear.

EXAMPLE 6

Predicted and Actual Results for Paracetamol

The three cell test equipment was operated with the release medium and at the pH described in Example 2. 500 mg of paracetamol was used.

The algorithm was used to match the $t_{max}$ and $t_{10}$ for paracetamol in vivo data (WO9739747, FIG. 4). $t_{max}$ and $t_{10}$ for in vivo data were 33 and 510 minutes respectively. The resulting residence times for the first, second and third cells were 7, 4.5, and 220 min respectively. F1, F2, F3, C1 vol, C2 vol and C3 vol were than calculated according to the guidelines described above, getting the following values: F1=0.0036 l/min; F2=0.0064/min; F3=0; C1 vol=0.025 l; C2 vol=0.045 l; C3 vol=2.69 l.

Figure 6:
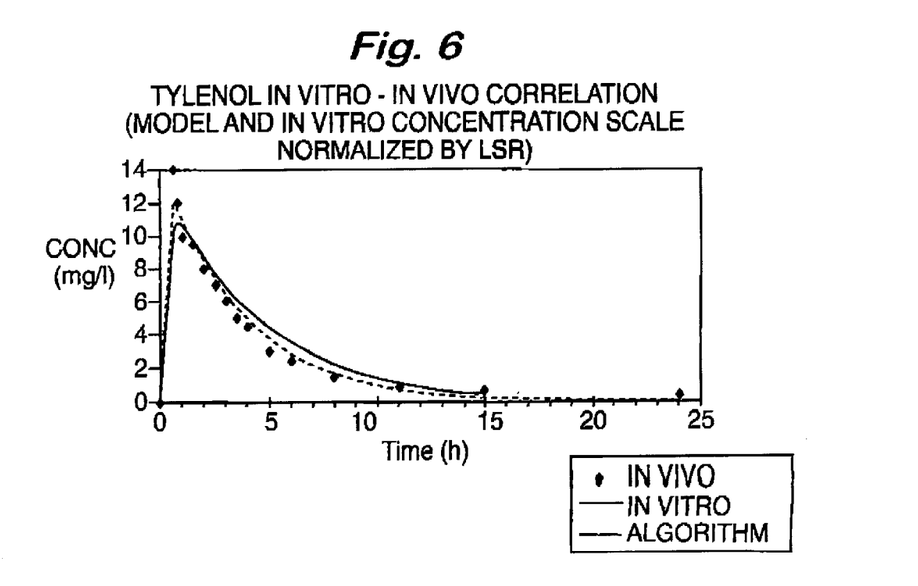
FIG. 6 is a graph showing the comparison of in vivo, predicted in vitro, and in vitro data for paracetamol (Tylenol®).

The data from this example is shown in FIG. 6. The data from the algorithm and the in vitro test has been adjusted using a linear scaling factor so that the data can be compared with the in vivo data. The excellent correlation between all three datasets is clear.

EXAMPLE 7

Predicted and Actual Results for Pseudoephedrine

The three cell test equipment was operated with the release medium and at the pH described in Example 2. 90 mg of pseudoephedrine was used.

The algorithm was used to match the $t_{max}$ and $t_{10}$ for pseuoephedrine in vivo data (EP1059084A2, FIG. 3). $t_{max}$ and $t_{10}$ for in vivo data were 90 and 1380 minutes respectively. The best fit with the algorithm gave $t_{max}$ and $t_{10}$ values of 89 and 1383 mins respectively. The resulting residence times for the first, second and third cells were, 18, 16, and 592 mins respectively. F1, F2, F3, C1 vol, C2 vol and C3 vol were than calculated according to the guidelines described above, getting the following values: F1=0.0022 l/min; F2=0.0047 l/min; F3=0; C1 vol=0.04 l; C2 vol=0.11 l; C3 vol=4.04 l.

Figure 7:
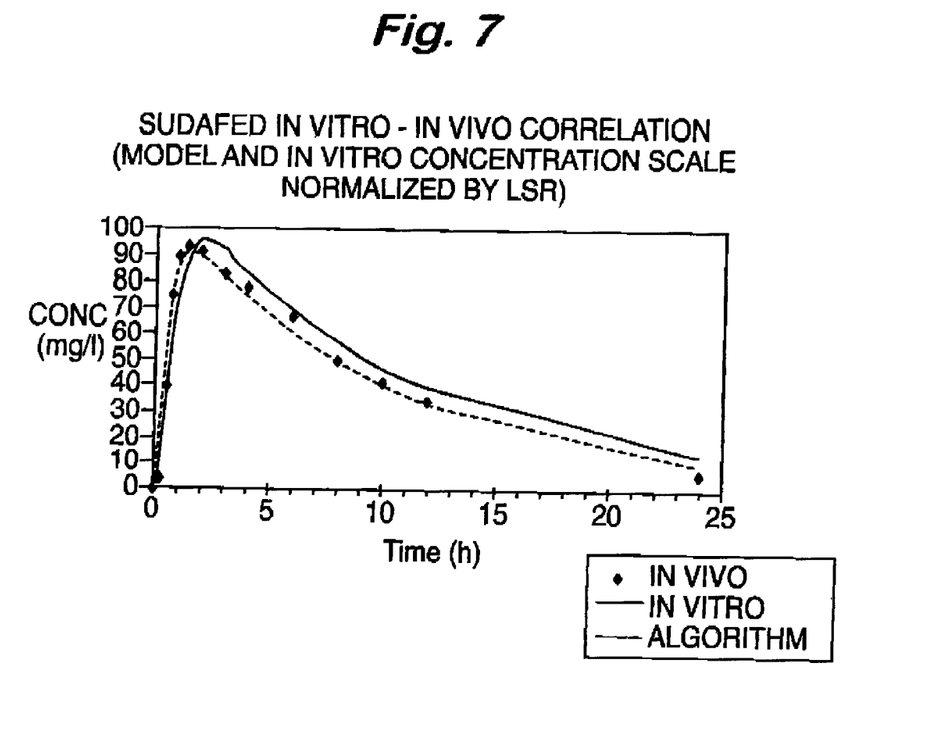
FIG. 7 is a graph showing the comparison of in vivo, predicted in vitro, and in vitro data for pseudoephedrine (Sudafed®).

The data from this example is shown in FIG. 7. The data from the algorithm and the in vitro test has been adjusted using a linear scaling factor so that the data can be compared with the in vivo data. The excellent correlation between all three data sets is clear.

Examples 5, 6, 7 demonstrate the excellent correlation between the dissolution profile predicted by the algorithm and the actual test results obtained from the test equipment.

I claim:

1. An apparatus for conducting dissolution tests comprising:
   a) two or more chambers connected in series;
   b) a supply of one or more media that can be continuously passed into said chambers;
   c) a means of analyzing the effluent from said chambers for substances of interest in the test;
   d) a means of controlling the temperature of the medium in said chambers;
   wherein said first chamber is capable of transferring solid particles to said second chamber;
   wherein said second chamber is capable of retaining solid;
   wherein said chambers have a means of adding test materials;
   wherein said chambers have a means of mixing the sample and medium;
   wherein said means of analyzing the effluent can be carried out at multiple times during the operation of the test equipment.

2. A dissolution test method for use with the apparatus of claim 1, comprising the steps of:
   a) passing one or more media through the chambers;
   b) adding the test sample to the first of said chambers;
   c) passing medium through said chambers such that any undissolved portion of the test sample is transferred from the first chamber into the second chamber;
   d) passing medium through said chambers such that any undissolved portion of the test sample remains in the second chamber;
   e) maintaining the temperature of the medium in said chambers at the desired temperature for the duration of the test;
   f) analyzing the effluent from said chambers to determine the concentration of substance dissolved from the test sample, wherein the data obtained from said test correlates with that obtained from in vivo plasma concentrations at Level A, as defined by the USFDA, without the use of a mathematical model.

3. A dissolution test method for use with the apparatus of claim 1 comprising the steps of:
   a) passing one or more release media through the cells;
   b) adding the test sample to the first of said cells;
   c) passing release medium through said cells such that any undissolved portion of the test sample is transferred from the first cell into the second cell;
   d) passing release medium through said cells such that any undissolved portion of the test sample remains in the second cell;
   e) maintaining the temperature of said cells at the desired temperature for the duration of the test;
   f) analyzing the effluent from said cells to determine the concentration of substance dissolved from the test sample, further provided that said test method can be used to predict the in vitro dissolution profile of a pharmaceutical active compound via the use of an algorithm comprising the steps of:
      (a) selecting values of residence times for flow through cells;
      (b) predicting the dissolution profile using an algorithm and said residence times;
      (c) comparing the predicted results from step (b) with in-vivo dissolution data;
      (d) estimating improved values of the residence times based on the comparison made in step (c);
      (e) repeating steps (a)–(d) until the comparison in step (c) meet acceptance criteria.

* * * * *